United States Patent [19]
Smithwick, Jr.

[11] 3,932,489
[45] Jan. 13, 1976

[54] PROCESS FOR T-BUTYLATING HYDROXY- OR THIOL-SUBSTITUTED AMINO ACIDS

[75] Inventor: Edward L. Smithwick, Jr., Indianapolis, Ind.

[73] Assignee: Eli Lilly and Company, Indianapolis, Ind.

[22] Filed: Nov. 16, 1973

[21] Appl. No.: 416,703

Related U.S. Application Data

[63] Continuation of Ser. No. 196,182, Nov. 5, 1971, abandoned.

[52] U.S. Cl........... 260/482 C; 252/433; 260/112.5; 260/326.2; 260/470; 260/471 C; 260/471 R; 260/481 C; 260/481 R; 260/482 R
[51] Int. Cl.².................................... C07C 125/06
[58] Field of Search......... 260/482 C, 482 P, 471 C, 260/481 C

[56] References Cited
OTHER PUBLICATIONS

Beyerman H. C. et al., Rec. Trav. Chem., 81 (691–698), 1962, Discussion on Method of Profec. Rep. Proceeding of the 5th European Symp., Oxford., September, 1962.

Primary Examiner—Anton H. Sutto
Assistant Examiner—Paul J. Killos
Attorney, Agent, or Firm—William C. Martens, Jr.; Everet F. Smith

[57] ABSTRACT

Hydroxy- or thiol-substituted amino acids are t-butylated by reacting them with isobutylene in the presence of a catalyst comprising boron trifluoride and anhydrous phosphoric acid.

8 Claims, No Drawings

PROCESS FOR T-BUTYLATING HYDROXY- OR THIOL-SUBSTITUTED AMINO ACIDS

This is a continuation, of application Ser. No. 196,182, filed Nov. 5, 1971, now abandoned.

BACKGROUND OF THE INVENTION

In prparing peptides by the interaction of the free amino group of one amino acid or peptide fragment with the free carboxyl group of another amino acid or peptide fragment, it is generally highly preferred that only those reactive functions which are intended to participate in the peptide formation be available during reaction. In other words, any other reactive groups which may be present in the reactants generally will be protected by prior reaction with an appropriate blocking group. Two such reactive functions which are sometimes present in amino acids or peptide fragments and which generally are protected prior to peptide chain building are the hydroxyl function and the thiol function. It has been found that protection of such groups can be achieved by reacting these functions with a suitable reagent to form the tertiary butyl ether or tertiary butyl thioether, respectively.

It is also quite possible that one would wish to protect a carboxyl group of an amino acid or peptide fragment. A tertiary butyl function provides a highly suitable protecting group for this purpose, producing the corresponding tertiary butyl ester. The tertiary butyl group is readily cleavable to re-form the free carboxyl group.

Literature describes the O-t-butylation of sterols using isobutylene when carried out in the presence of a catalyst comprising boron trifluoride etherate and anhydrous phosphoric acid, see H. C. Beyerman and G. J. Heiszwold, *Rec. Trav. Chim.*, 84, 203 (1965). In this publication the use of the catalyst was directed exclusively to O-t-butylation of sterols. No indication or direction is contained in this publication with respect to the t-butylation of hydroxyl groups, thiol groups, or carboxyl groups present in amino acids.

The customary method by which an amino acid or peptide fragment has been esterified, etherified, or thioetherified using isobutylene has been by reacting the acid or peptide fragment with isobutylene in the presence of sulfuric acid as catalyst. Using a sulfuric acid catalyst system, it has been found to be necessary to carry out the reaction over an extended period of time, sometimes lasting even for several days. Since the reaction takes such a long period of time, it is furthermore essential, in order to retain the presence of the isobutylene reactant, to carry out the reaction in a pressure bottle. Moreover, typically the reaction does not proceed to completion. For example, using L-serine as amino acid, in which it is intended that the amino acid be both esterified at the carboxyl group and etherified at the hydroxyl group, it is found that a large portion of the product which results is the t-butyl ester of the amino acid containing intact a free hydroxyl function. That is to say, the conditions of reaction are such that it is possible to esterify the amino acid but not to accomplish substantial etherification. Thus, the sulfuric acid catalyzed t-butylation of hydroxy or thiol amino acids, although suitable for achieving some etherification, nevertheless, exhibits serious limitations.

SUMMARY OF THE INVENTION

It has now been found to be possible to accomplish the t-butylation of hydroxy or thiol amino acids using much shorter reaction times while avoiding the need for a pressure bottle and producing a much cleaner product in terms of extent of t-butylation. This invention involves a process for the t-butylation of hydroxy amino acids or thiol (sulfhydryl) amino acids using isobutylene, and is accomplished by carrying out the reaction in the presence of a catalyst comprising boron trifluoride and anhydrous phosphoric acid.

Accordingly, this invention is directed to a process for t-butylating a hydroxy or thiol amino acid, which comprises reacting a hydroxy or thiol amino acid, an ester thereof, or an N-protected derivative thereof, with isobutylene in the presence of a catalyst comprising boron trifluoride and anhydrous phosphoric acid.

DETAILED DESCRIPTION OF THE INVENTION

This invention is directed to a process for preparing tertiary butyl ethers of hydroxy amino acids or thiol amino acids. The amino acid which can be used in the process of this invention is any amino acid which has in its structure a free hydroxyl or a free thiol functional group. Preferably, the amino acid which is employed will have the following structure:

$$R-CH-(CH_2)_n-\overset{O}{\underset{}{C}}-OH$$
$$\underset{NHZ}{|}$$

In the above formula $n$ is 0 or an integer from 1 to 3, Z is hydrogen or an amine protecting group, R is 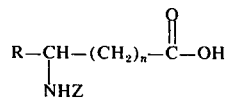 or 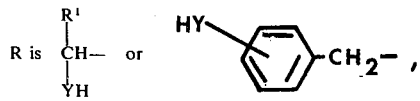, wherein $R^1$ is hydrogen, methyl, ethyl or propyl, Y is oxygen or sulfur, and R and Z when taken together are

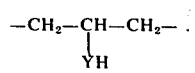

Esters of the above structure can likewise be readily employed in the process of this invention. The structure of the alcohol moiety of the ester is not important except that the alcohol moiety be stable under the conditions of t-butylation. The process of this invention thus contemplates the use of amino acid ester derivatives having virtually any of the commonly recognized ester functions. Such ester functions include, but are not limited to, for example, $C_1$–$C_5$ alkyl, benzyl, p-nitrobenzyl, 2,2,2-trihaloethyl, $C_5$–$C_7$ cycloalkyl, and the like.

In the event that the amino acid is in the form of the free acid, the process of this invention will also result in the product of the t-butyl ester of the amino acid, thus producing a t-butylation not only at the free hydroxyl or free thiol function, but also at the free carboxyl function present in the molecule.

In carrying out the reaction of the process of this invention, it is highly preferred that the amino group of the amino acid reactant be blocked with a suitable protecting group, many of which are well known in the art. However, it is not essential that such protecting group be used, and the reactant can indeed be an amino acid having a free amino group. By "protecting group" in the above definition, therefore, is meant any of the well recognized amino protecting groups, which include, but are not limited to, for example, benzyloxycarbonyl, t-butoxycarbonyl, cycloalkyloxycarbonyl, adamantyloxycarbonyl, and the like.

As used herein, the term "halo" includes fluorine, chlorine, bromine and iodine.

Typical of the amino acids or derivatives thereof which can be used as reactants in the process of this invention are, for example, serine, threonine, cysteine, hydroxyproline, tyrosine, and the like. Amino acids of varying other structures may likewise be used, the only requisite being that the amino acid contain a free hydroxyl or thiol (sulfhydryl) group. Thus, the hydroxyl or sulfhydryl group may be joined to a carbon atom present in an alkyl or cycloalkyl group, an aromatic group, or a heterocyclic nucleus.

The reaction can be carried out in any convenient manner. Generally, the amino acid or appropriately blocked derivative thereof is dissolved or suspended in a suitable inert liquid medium. The catalyst, comprising a mixture of boron trifluoride and anhydrous phosphoric acid, is added to the amino acid-containing mixture, followed by an appropriate quantity of cooled isobutylene. The reaction is then permitted to proceed for an appropriate period of time, and the product is isolated according to known techniques.

Suitable liquid media for carrying out the reaction include any liquid system which is inert to the reaction and which will readily dissolve isobutylene. Such liquid media include, for example, methylene chloride, tetrahydrofuran, N,N-dimethylformamide, benzene, toluene, ethyl ether, acetonitrile, and the like. The amino acid or peptide fragment can be present as a suspension in the liquid medium or can be dissolved therein. Normally, the solvent will be present in an amount sufficient to readily dissolve the isobutylene reactant. It is also possible to carry out the reaction in the absence of any added solvent or liquid medium, employing only cooled excess isobutylene as the reaction medium.

The catalyst which is employed in the process of this invention can be prepared prior to the reaction or can be prepared in situ. The catalyst comprises a combination of boron trifluoride and anhydrous phosphoric acid. The boron trifluoride can be present in the form of its etherate complex. The amount of boron trifluoride or boron trifluoride etherate relative to the anhydrous phosphoric acid can range from about 3:1 to about 1:3 on a molar basis. Generally, however, the molar of boron trifluoride or etherate (calculated as free boron trifluoride) to anhydrous phosphoric acid will be from about 2:1 to about 1:1.

In carrying out the reaction in accordance with the process of the invention, the combined boron trifluoride-anhydrous phosphoric acid will be employed in a catalytic amount which generally will be within the range of from about 5 to about 30 grams per mole of the amino acid reactant.

When the catalyst is to be prepared prior to its use in the t-butylation reaction, this can be accomplished by introducing an appropriate amount of boron trifluoride gas into the anhydrous phosphoric acid. Alternatively, the boron trifluoride etherate complex can be prepared by interaction of ethyl ether with boron trifluoride, and an appropriate amount of the etherate can be mixed with the anhydrous phosphoric acid. In accomplishing this mixing, the etherate can be added to the phosphoric acid or the phosphoric acid can be added to the etherate.

When it is desired to prepare the catalyst in situ, such preparation can be carried out using the techniques described above. That is, an appropriate amount of the boron trifluoride etherate can be added to the reaction mixture followed by the anhydrous phosphoric acid, or the anhydrous phosphoric acid can be added to the reaction mixture followed by an appropriate quantity of the boron trifluoride etherate. Likewise, boron trifluoride gas can be employed, and in such an instance the boron trifluoride gas can be bubbled into the reaction mixture either before or after addition of the anhydrous phosphoric acid.

Anhydrous phosphoric acid can be conveniently prepared by adding to a commercially available phosphoric acid sufficient phosphorus pentoxide to react with all of the water present in the commercial grade phosphoric acid and thereby to produce a 100 percent (anhydrous) phosphoric acid.

The isobutylene which is employed need be present only in an amount sufficient to react with each of the functional groups which are to be t-butylated. Thus, if the amino acid which is to be t-butylated contains both a free carboxyl group and a free hydroxyl or thiol group, two moles of the isobutylene will be required per mole of the amino acid. Normally, however, in order to assure the presence and retention of a sufficient amount of isobutylene in the reaction mixture, a substantial excess of the isobutylene is employed. Generally, therefore, from about 4 to about 30 moles of the isobutylene is used per mole of amino acid. This is especially true when the reaction is carried out at atmospheric pressure and at a temperature which permits the free exiting of isobutylene from the reaction mixture.

The reaction normally is carried out at atmospheric pressure and, therefore, under conditions which permit the isobutylene to freely exit from the reaction system. However, it is also possible to carry out the reaction in a closed system, such as in a pressure bottle, with the pressure build-up being achieved by reason of the vapor pressure of the isobutylene itself.

The temperature at which the reaction is carried out is not critical except by reason of the limitations imposed by the isobutylene itself. Normally, the reaction will be carried out at a temperature from about −30°C. to about room temperature. It is preferred that the reaction be carried out at a temperature within the range from about −20°C. to about 0°C.

In accordance with this invention, the reaction time is significantly reduced over that customarily experienced by previous t-butylation reactions. The time for completion of the reaction will depend upon the particular amino acid or derivative thereof which is employed as well as the temperature at which the reaction is carried out. However, normally, the reaction will be complete within about two to about eight hours.

As hereinbefore mentioned, the process of this invention permits the ready t-butylation of hydroxy- or thiol-containing amimo acids. This invention permits a more complete extent of reaction and the use of a milder set of reaction conditions in terms of time of reaction and pressure at which the reaction can be carried out.

It has been recognized that it is somewhat more difficult to accomplish the etherization of the hydroxyl or sulfhydryl function on the amino acid than it is to accomplish the esterification of the carboxyl function. Thus, the known methods of carrying out the t-butylation resulted in extensive esterification but only moderate etherification. Many times, therefore, the resulting product comprised a mixture of major proportions of the ester containing a free hydroxyl or sulfhydryl function and the desired product, namely the ester containing the t-butylated hydroxyl or sulfhydryl function. Separation problems which thereby resulted were many times insurmountable.

In order to present a picture of the problems which exist in the previously known method when compared with the process of this invention, the following comparative example is provided. It employs the typical sulfuric acid catalyst technique. Following this comparative example are several examples which illustrate the process of this invention and demonstrate the improvement available therefrom.

COMPARATIVE EXAMPLE t-Butylation of N-Benzyloxycarbonyl-Threonine

About 16.2 g. of N-benzyloxycarbonyl-threonine, 50 ml. of methylene dichloride, and 40 ml. of isobutylene were placed in a cooled pressure bottle. About 0.2 ml. of concentrated sulfuric acid was added, the bottle was sealed, and the reaction mixture was shaken at room temperature for about 16 hours. At the end of this reaction period the pressure was released and a stream of dry nitrogen was passed through the resulting clear solution for a period of about 0.5 hour. The reaction mixture was then washed with 5 percent aqueous sodium bicarbonate, dried over sodium sulfate, and the solvent was evaporated. A yellow oil remained. The yellow oil was dissolved in about 100 ml. of methanol, and a water slurry of 3 g. of 5 percent palladium on carbon was added. The reaction mixture was stirred and flushed with nitrogen for about 10 minutes, after which hydrogen was bubbled into the reaction mixture for about 6.5 hours. The reaction mixture was then filtered, and the filtrate was concentrated by evaporation of the solvent. The residual oil was dissolved in about 100 ml. of ethyl ether, and about 17.8 g. of dibenzenesulfonamide was added. The mixture was cooled, and a precipitate formed which was filtered off and purified by refluxing it in ethyl ether. The substance which was obtained weighed about 20 g., and had a m.p. of 82°–3°C. By thin layer chromatography (TLC), this substance was shown to be a mixture of major amounts of the dibenzenesulfonamide amine salts of t-butyl threoninate and t-butyl (O-t-butyl) threoninate.

In the following examples, the optical rotations which are provided were taken on a Rudolph Model 220 polarimeter. Thinlayer chromatograms (TLC) were run on E. M. Laboratories Pre-Coated TLC Places Silica Gel F-254 and were developed with minhydrin or chloride-O-tolidine reagents.

EXAMPLE I

Preparation of Benzyl N-Benzyloxycarbonyl-(O-t-Butyl) Serinate

Benzyl N-benzyloxycarbonylserinate in an amount of 32.9 g. (0.1 mole) was dissolved in 125 ml. of methylene chloride. The solution was cooled to about −15°C. and 2.5 ml. of boron trifluoride etherate followed by 1 ml. of 100 percent $H_3PO_4$ (prepared from 25 g. of $P_2O_5$ added to 33 g. (19.5 ml.) of 85 percent phosphoric acid) were added. To the resulting mixture was then added about 125 ml. of liquid isobutylene. The reaction mixture was stirred at about −15°C. for about 15 minutes, and the mixture was then warmed to about 0°C. and maintained thereat for about 2 hours. Cooling was then discontinued, and the reaction mixture was maintained without cooling for about 2 hours. The reaction mixture was then cooled in an ice bath to about 0°C. and 100 ml. of 2N $NH_4OH$ was added. The reaction mixture was stirred for about 5 to 10 minutes at about 0°C. and was then poured into about 600 ml. of ethyl ether. An aqueous layer and an organic layer formed, and the aqueous layer was separated from the organic layer. The aqueous layer was extracted with ether, and the ether extract was added to the organic layer. The organic layer was washed first with water, then with a saturated sodium chloride solution, and then was dried over magnesium sulfate. Evaporation of the solvent produced a residual oil. The oil was dissolved in a mixture of ethyl acetate and petroleum ether, and the solution was cooled in a dry ice/acetone bath to produce 27.7 g. of benzyl N-benzyloxycarbonyl-(O-t-butyl) serinate, m.p., 48°–9° C. Optical rotation, $[\alpha]_D^{24}$ −13.4. TLC $R_f$ value — in n-heptane/t-butyl alcohol/pyridine (5:1:1)—0.4; in chloroform/acetic acid (9:1)—0.7.

Analysis, Calc. for $C_{22}H_{27}NO_5$: C, 68.50; H, 7.06; N, 3.65. Found: C, 68.29; H, 6.85; N, 3.70.

EXAMPLE II

Preparation of p-Nitrobenzyl N-Benzyloxycarbonyl-(O-t-Butyl) Threoninate

Using the procedure described in Example I, 38.8 g. (0.1 mole) of p-nitrobenzyl N-benzyloxycarbonyl-threoninate were reacted with isobutylene in the presence of boron trifluoridephosphoric acid catalyst. A residue of product was obtained which was recrystallized from a mixture of ethyl acetate and petroleum ether to produce a total of about 34 g. of p-nitrobenzyl N-benzyloxy-carbonyl-(O-t-butyl)threoninate, m.p., 54°–6°C. Optical rotation $[\alpha]_D^{24}$ +11.0. TLC showed the presence of a trace of the starting material in the product and gave an $R_f$ value of 0.5 in n-heptane/t-butyl alcohol/ pyridine (5:1:1).

Analysis, Calc. for $C_{23}H_{28}N_2O_7$: C, 62.15; H, 6.35; N, 6.30. Found: C, 61.96; H, 6.16; N, 6.25.

EXAMPLE III

Preparation of t-Butyl (O-t-Butyl)Serinate Dibenzenesulfonamide Amine Salt

Using the procedure described in Example I, 23.9 g. (0.1 mole) of N-benzyloxycarbonyl serine was reacted with isobutylene, in the presence of boron trifluoridephosphoric acid catalyst.

An oily residue product was obtained which was dissolved in about 300 ml. of methanol containing about 3 g. of 5 percent palladium on carbon catalyst. Nitrogen was bubbled into the mixture for about 10 minutes, and the mixture was cooled to about 0°C. Hydrogen was then bubbled into the cooled mixture and vented to the atmosphere through a barium hydroxide trap. The addition of hydrogen was continued until no more precipitate appeared in the trap, evidencing a disappearance of carbon dioxide in the exit gases. Hydrogen addition was continued for an additional 0.5 hour at 0°C. The catalyst was then filtered from the reaction mixture, and the filtrate was evaporated in vacuo. The residue was dissolved in about 100 ml. of ethyl ether, and 29.7 g. (0.1 mole) of dibenzenesulfonamide dissolved in 500 ml. of ethyl ether was added. Precipitation followed immediately. The product was collected by filtration, washed with cold ether, and dried in vacuo. About 44.8 g. of the dibenzenesulfonamide amine salt of t-butyl (O-t-butyl)serinate, m.p., 161°–2°C., was collected. Optical rotation $[\alpha]_D^{24}$ +2.6; TLC $R_f$ value, in sec-butanol/3% ammonium hydroxide (3:1)—0.7; in n-heptane/t-butyl alcohol/acetic acid/water/pyridine (25:50:6:24:20)—0.2.

Analysis, Calc. for $C_{23}H_{34}N_2O_7S_2$: C, 53.68; H6.66; N, 5.44; S, 12.46. Found: C, 53.38; H, 6.59; N, 5.14; S, 12.76.

EXAMPLE IV

Preparation of t-Butyl (O-t-Butyl)Threoninate Dibenzenesulfonamide Amine Salt

About 38.2 g. (0.15 mole) of N-benzyloxycarbonyl threonine was suspended in 250 ml. of methylene chloride. The resulting mixture was cooled to about −15°C., and to this mixture was added 5 ml. of boron trifluoride etherate, 2.1 ml. of 100 percent phosphoric acid, and about 250 ml. of cold isobutylene. The reaction mixture was maintained at about −15°C. for about 1.5 hours, after which the temperature was raised to about 0°C. and maintained thereat for about an additional 1.5 hours. Cooling was discontinued, and the reaction mixture was maintained without cooling for about one hour. About 250 ml. of aqueous 2N ammonium hydroxide was then added, the reaction mixture was stirred, and about 250 ml. of ethyl ether was added. The resulting mixture comprised an aqueous and an organic phase. The aqueous phase was separated from the organic phase, and the organic phase was washed with aqueous 2N ammonium hydroxide. The organic phase was then dried over magnesium sulfate and the solvent removed in vacuo to produce an oily residue.

The oily residue was suspended in about 300 ml. of methanol, and about 5 g. of 5 percent palladium on carbon was added. Nitrogen was bubbled into the mixture for about 10 minutes, and the mixture was cooled to about 0°C. Hydrogen was then bubbled through the reaction mixture for about 4 hours. The methanol was then evaporated from the mixture, and about 100 ml. of ethyl ether was added, followed by about 44.5 g. of dibenzenesulfonamide dissolved in 600 ml. of ethyl ether. A precipitate formed immediately and was collected by filtration to yield about 60.6 g. of the dibenzenesulfonamide amine salt of t-butyl (O-t-butyl)-threoninate, m.p., 85°–7°C. Optical rotation $[\alpha]_D^{24}$ −4.7. By TLC the product exhibited an $R_f$ value in sec-butanol/3% ammonium hydroxide (3:1)—0.7; in n-heptane/t-butyl alcohol/acetic acid/water/pyridine (25:50:6:24:20)—0.4.

Analysis, Calc. for $C_{24}H_{36}N_2O_7S_2$: C, 54.52; H, 6.86; N, 5.30; S, 12.13. Found: C, 54.42; H, 7.09; N, 5.44; S, 12.15.

I claim:
1. A process for t-butylating a hydroxy or thiol amino acid, which comprises reacting a hydroxy or thiol amino acid, an ester thereof, or an N-protected derivative thereof, with isobutylene in the presence of a catalyst consisting essentially of boron trifluoride and anhydrous phosphoric acid.

2. The process of claim 1, in which the hydroxy or thiol amino acid reactant has the formula

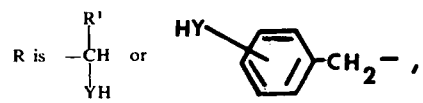

in which n is 0 or an integer from 1 to 3, Z is hydrogen or an amine protecting group,

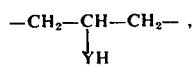

wherein $R^1$ is hydrogen, methyl, ethyl, or propyl, Y is oxygen or sulfur, and R and Z when taken together are

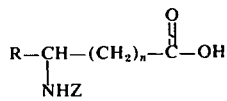

or the reactant is an ester of the above acid.

3. The process of claim 2, in which the t-butylation is carried out at atmospheric pressure in the presence of an inert solvent and at a temperature of from about −30°C. to about room temperature.

4. The process of claim 3, in which the t-butylation is conducted for a period of from about 2 to about 8 hours.

5. The process of claim 2, in which Z is benzyloxycarbonyl, t-butoxycarbonyl, cycloalkyloxycarbonyl, or adamantyloxycarbonyl.

6. The process of claim 2, in which an ester is employed as reactant, said ester having an alcohol moiety $C_1$–$C_5$ alkyl, benzyl, p-nitrobenzyl, 2,2,2-trihaloethyl, or $C_5$–$C_7$ cycloalkyl.

7. The process of claim 2, in which n is 0, and R is —$CH_2OH$.

8. The process of claim 2, in which n is 0 and R is

* * * * *